(12) United States Patent
Merker et al.

(10) Patent No.: US 10,556,850 B1
(45) Date of Patent: Feb. 11, 2020

(54) PROCESS FOR THE PURIFICATION OF ACROLEIN

(71) Applicant: Evonik Degussa GmbH, Essen (DE)

(72) Inventors: Thorsten Merker, Erftstadt (DE); Martin Koerfer, Kahl (DE); Michael Eicker, Bergisch Gladbach (DE); Bruno Krudewig, Bonn (DE); Rainer Malzkorn, Grosskrotzenburg (DE); Haohao Zhu, Euskirchen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 16/520,384

(22) Filed: Jul. 24, 2019

(30) Foreign Application Priority Data

Jul. 30, 2018 (EP) .................................... 18186207

(51) Int. Cl.
*C07C 45/82* (2006.01)
*C07C 319/00* (2006.01)
*C07C 319/06* (2006.01)
*C07C 321/08* (2006.01)
*C07C 47/22* (2006.01)

(52) U.S. Cl.
CPC ............ *C07C 45/82* (2013.01); *C07C 319/06* (2013.01); *C07C 47/22* (2013.01); *C07C 321/08* (2013.01)

(58) Field of Classification Search
CPC .............................. C07C 45/82; C07C 319/06
See application file for complete search history.

(56) References Cited

U.S. PATENT DOCUMENTS

| 6,515,187 B1 | 2/2003 | Shon et al. |
| 2005/0103616 A1 | 5/2005 | Gros |

OTHER PUBLICATIONS

Extended European Search Report dated Jan. 22, 2019, in Patent Application No. 18186207.9, 5 pages.

*Primary Examiner* — Sikarl A Witherspoon
(74) *Attorney, Agent, or Firm* — Oblon, McClelland, Maier & Neustadt, L.L.P.

(57) ABSTRACT

The present invention relates to a process for purifying acrolein. The process includes the steps of a) splitting a liquid feed stream containing acrolein into at least a first liquid stream and a second liquid stream, b) introducing the first liquid stream with a temperature T1 into a distillation column at a point between the top and the bottom of the distillation column, c) introducing the second liquid stream with a temperature T2 into the distillation column at the top of the distillation column, d) withdrawing an overhead vapor stream enriched in acrolein from the distillation column, and e) withdrawing a bottom stream depleted in acrolein. The temperature T2 of the second liquid stream in step c) is lower than the temperature T1 of the first liquid stream in step b).

15 Claims, 4 Drawing Sheets

PROCESS FOR THE PURIFICATION OF ACROLEIN

FIELD OF THE INVENTION

The present invention relates to a process for the purification of acrolein. Further, the present invention also relates to a process for the preparation of 3-mercaptopropionaldehyde by reacting the acrolein obtained from the purification process with methyl mercaptan, the hemithioacetal of methyl mercaptan and 3-methylthiomercaptopropionaldehyde and/or a mixture thereof.

BACKGROUND OF THE INVENTION

Acrolein is typically prepared in a partial gas phase oxidation of propene in the presence of a heterogeneous catalyst. The thus obtained acrolein containing product gas mixture also contains inert or non-condensable gases, such as nitrogen, oxygen, carbon monoxide, carbon dioxide, propylene or propane and by-products such as acetic acid, formaldehyde, allyl alcohol, and mainly acrylic acid. Subsequent treatments are therefore necessary to improve the purity of the crude acrolein. In a first treatment, the acrolein containing product gas mixture from the partial gas phase oxidation is fed to a quench column or quencher, where the heavy boilers, such as acetic acid and acrylic acid, are removed. A gas stream enriched in acrolein leaves the quencher. In the second treatment, the acrolein is separated from the gas stream leaving the quencher by absorption in water using an absorption column, at the bottom of which an aqueous acrolein solution is collected. In the third and final treatment, the aqueous acrolein solution is fed to a distillation column, where the low boiling acrolein is separated from the high boiling absorption medium and is recovered in liquid form.

A distillation is a separation unit, which utilizes vapor and liquid phases at essentially the same temperature and pressure for the coexisting zones. Within a distillation column means such as random or structured packings, and plates of trays are used to bring the two phases into intimate contact. Trays are stacked one above the other and enclosed in a cylindrical shell to form a column. Packings are also generally contained in a cylindrical shell between hold-down and support plates. A stream containing the compound to be purified is introduced into the distillation column at a single point between the top and the bottom of the distillation column, the so-called feed stage. This point also subdivides the distillation column into a rectifying section above the feed stage and a stripping section below the feed stage. The column may be operated continuously or in batch mode depending on a number of factors such as scale and flexibility of operations and solids content of feed. Because of the difference in density between vapor and liquid phases, liquid runs down inside the column, cascading from tray to tray, while vapor flows up the column, contacting liquid at each tray or within the packing. Liquid reaching the bottom of the column is partially vaporized in a heated reboiler to provide boil-up, which is sent back to the column. The remainder of the bottom liquid is withdrawn as bottoms, bottom stream or bottom product. Vapor reaching the top of the column is cooled and condensed to liquid in the overhead condenser. Part of this liquid is fed back to the column as reflux to provide liquid overflow. The remainder of the overhead stream is withdrawn as distillate, or overhead product. This overall flow pattern in a distillation column provides countercurrent contacting of vapor and liquid streams on all of the trays through the column. Vapor and liquid phases on a given tray approach thermal, pressure, and composition equilibria to an extent dependent upon the efficiency of the contacting tray. The lighter components, i.e. the components with lower boiling temperatures, tend to concentrate in the vapor phase, while the heavier components, i.e. the components with higher boiling temperatures, concentrate in the liquid phase. The result is a vapor phase that becomes richer in lighter components as it passes up the column and a liquid phase that becomes richer in heavier components as it cascades downwards. The overall separation achieved between the distillate and the bottoms depends primarily on the relative volatilities of the components, the number of contacting trays in each column section, and the ratio of the liquid-phase flow rate to the vapor-phase flow rate in each section.

However, the person skilled in the art is faced with several big problems when purifying an aqueous acrolein solution in a standard distillation procedure. The first problem is that the condensation of the overhead vapor and its return to the top of the distillation column as reflux lead to a large holdup of the toxic compound acrolein in liquid and concentrated form within the distillation apparatus. Meaningful parameters for the evaluation of the toxicity of a chemical compound are amongst others the so-called ERPG (emergency response planning guidelines) values. ERPGs are exposure guidelines designed to anticipate health effects from exposure to certain airborne chemical concentrations. A chemical may have up to three ERPG values, each of which corresponds to a specific tier of health effects. The three ERPG tiers are defined as follows: a) ERPG-3 is the maximum airborne concentration below which nearly all individuals could be exposed for up to 1 hour without experiencing or developing life-threatening health effects, b) ERPG-2 is the maximum airborne concentration below which nearly all individuals could be exposed for up to 1 hour without experiencing or developing irreversible or other serious health effects or symptoms which could impair an individual's ability to take protection action, and c) ERPG-1 is the maximum airborne concentration below which nearly all individuals could be exposed for up to 1 hour without experiencing more than mild, transient adverse health effects or without perceiving a clearly a clearly defined objectionable odor. Accordingly, the lower the ERPG values for a chemical compound, the higher is the risk potential of said chemical compound. With ERPG values of 0.05 ppm (ERPG-1), 0.15 ppm (ERPG-2) and 1.5 ppm (ERPG-3), acrolein is among the chemicals with the highest risk potential. Its storage therefore should be avoided and the holdup of acrolein in a plant also should be kept as low as possible. The second problem often faced in purifying an aqueous acrolein solution by distillation are polymerization and fouling. This fouling is due to the deposition of a solid phase resulting from the polymerization of compounds such as acrylic acid and allylacrylate, or even acrolein itself.

For minimizing the presence of liquid acrolein and fouling, the published patent application US 2005/0103616 A1 teaches a process for the purification of acrolein, in which an aqueous solution containing 6 wt.-% of acrolein is introduced into a distillation column equipped at its base with at least one boiler and at its top with at least one condenser. A liquid, water comprising mixture is withdrawn at the base of the distillation column as bottom stream, and an acrolein comprising gas mixture is withdrawn at the top of the distillation column as overhead vapor stream. This overhead vapor stream contains from 30 to 70 vol.-% of water. It is therefore necessary to subject said overhead vapor stream to a further process step in order to provide for purified acrolein. In this further process step the overhead vapor stream withdrawn from the distillation column is fed to a (partial) condenser, where the overhead vapor stream is cooled to a temperature, which makes it possible to obtain an aqueous condensate, which is fed back as reflux to the top of the distillation column, and an acrolein-rich gas mixture. However, the thus obtained aqueous condensate still contains ca. 20 wt.-% of acrolein. The additional use of the (partial) condenser, therefore, leads to a relatively large total holdup of acrolein, in particular liquid acrolein, in the distillation apparatus as a whole, and in particular in said condenser. However, in a given apparatus like a column or an external condenser connected to a column the total hold of a toxic compound, in particular in liquid form, should be kept as low as possible—a requirement which the process of US 2005/0103616 A1 does not meet. Further disadvantages of this process are the increased energy demand for operating the additional condenser and increased complexity of the used apparatus.

Hence, there was a need for an improved process for the purification of acrolein, which reduces the holdup of concentrated liquid acrolein in the distillation apparatus, in particular in the distillation column.

SUMMARY OF THE INVENTION

It was found that this problem is solved in that the overhead vapor stream enriched in acrolein, which is obtained in the distillation of an acrolein containing feed stream, is not liquefied in a condenser or external heat exchanger, as in standard distillation processes. Accordingly, there is no external reflux of a liquefied overhead stream back to the top of the distillation column. Rather, the acrolein containing feed stream is fed to a special distillation process, which in contrast to standard distillation processes involves the splitting of the acrolein containing liquid feed stream (1) into at least two streams (2) and (3). The stream (2) is introduced with a temperature T1 into the distillation column at a point between the top and the bottom of the distillation column. In addition to said stream (2), an optional further stream, also split from the feed stream (1), can be introduced into the distillation column at a point between the top and the bottom of the distillation column, which is different from the point of introduction of stream (2). The stream (3) is introduced with a temperature T2 into the distillation column at the top of said distillation column (4). In order to provide for the liquid overflow, which is necessary to achieve the purification, in particular with a specific degree of purification, the temperature T2 of the stream (3) upon introduction into the distillation column is lower than the temperature T1 of the stream (2) and any optional further stream upon introduction into the distillation column. A bottom stream depleted in acrolein is withdrawn from the sump of the distillation column, and a vapor stream enriched in acrolein is finally withdrawn from the distillation column as overhead vapor stream.

An object of the present invention is therefore a process for the purification of acrolein, comprising the steps of
a) splitting a liquid feed stream (1) comprising acrolein into at least a first liquid stream (2) and a second liquid stream (3),
b) introducing the first liquid stream (2) with a temperature T1 into a distillation column (4) at a point between the top and the bottom of the distillation column,
c) introducing the second liquid stream (3) with a temperature T2 into the distillation column (4) at the top of the distillation column,
d) withdrawing an overhead vapor stream (5) enriched in acrolein from the distillation column (4), and
e) withdrawing a bottom stream (6) depleted in acrolein from the distillation column (4),
wherein the temperature T2 of the stream (3) in step c) is lower than the temperature T1 of the stream (2) in step b).

DETAILED DESCRIPTION OF THE INVENTION

It was found that the purification process according to the present invention leads to a significantly reduced accumulation of the by-products allylalcohol and allylacrylate. As a further consequence, there is no fouling or at least less fouling in the distillation column used.

In addition, the process according to the present invention also leads to significant savings in the energy input for the operation of the distillation column (4), compared to a process for the purification of acrolein, which is performed in a standard distillation column of the prior art. Specifically, it was found that the process according to the present invention reduces the reboiler duty of the distillation column (4) by a factor of up to ca. 16%, compared to a process for the purification of acrolein, which is performed in a standard distillation column of the prior art.

The distillation column used in the process according to the present invention comprises at least one boiler or reboiler, which provides the energy required for evaporating the components in the distillation column.

Regarding the distillation column as such, the purification process according to the present invention is not limited to a specific type of distillation column. Rather, said distillation column can be a trayed column, a packed column, or a column with a structured packing.

The acrolein comprising liquid feed stream (1) of step a) comes from an acrolein absorption column, where acrolein is absorbed in water. Therefore, the acrolein comprising liquid feed stream (1) is an aqueous acrolein comprising liquid feed stream (1). Accordingly, the first liquid stream (2) and the second liquid (3) as well as any optional further stream, which is also split from the acrolein comprising liquid feed stream (1) are also aqueous acrolein comprising liquid streams. The process according to the present invention is not limited regarding the concentration of specific components, in particular acrolein, in this liquid feed stream (1). The same necessarily applies to the first liquid stream (2) and the second liquid stream (3) and any further stream, split from said liquid feed stream (1). Since the acrolein comprising liquid feed stream (1) typically comes from an acrolein producing process and in particular from an acrolein absorption column, said liquid feed stream (1) preferably comprises from 5 to 7 wt.-% of acrolein, A typical acrolein comprising liquid feed stream (1) from large scale processes comprises ca. 93 wt.-% water, ca. 6 wt.-% acrolein, ca. 0.2 wt.-% formaldehyde, ca. 0.2 wt.-% of acrylic acid, 0.1 wt.-% acetaldehyde, 0.1 wt.-% of allylalcohol, and traces of carbon dioxide, allylacrylate and nitrogen.

The splitting of the liquid feed stream (1) also allows an adjustment of the fractions of each of the liquid streams (2) and (3) as well as of any other stream, which is introduced into the distillation column in addition to the first liquid stream (2). The chosen flow rates of the thus obtained first liquid stream (2), the second liquid stream (3) and any optional further liquid streams in addition to the first liquid stream (2) correspond to the desired mass fraction for these streams. The total of the first liquid stream (2) and the second liquid stream (3) as well as of any liquid stream in addition to the first liquid stream (2) equals the input flow of the liquid feed stream (1). Hence, the splitting of the liquid feed stream (1) also allows to adjust a specific mass flow ratio of the first liquid stream (2) to the second liquid stream (3).

It was found that a mass flow ratio of the first liquid stream (2) to the second liquid stream (3) in the range of from 95:5 to 50:50 is not only suitable to achieve a degree of separation which is equal or at least comparable to the processes of the prior art. Rather, the process according to the present invention also saves the complete or at least part of the energy-input of a prior art distillation process for the condensation of the vapor reaching the top of the distillation column and the evaporation of the condensed vapor, which is fed back to the distillation column as reflux. Already a small second liquid stream (3) relative to the first liquid stream (2) is sufficient to achieve a purification of acrolein with an identical or at least comparable degree of quality as in a prior art distillation procedure. In the process according to the present invention the mass flow ratio of the first liquid stream (2) to the second liquid stream (3) preferably ranges from 95:5 to 50:50, from 90:10 to 50:50, from 85:15 to 50:50, from 80:20 to 50:50, from 75:25 to 50:50, from 70:30 to 50:50, from 65:35 to 50:50, from 60:40 to 50:50 or from 55:45 to 50:50.

In an embodiment of the purification process according to the present invention the mass flow ratio of the first liquid stream (2) to the second liquid stream (3) ranges from 95:5 to 50:50.

It was further found that a mass flow ratio of the first liquid stream (2) to the second liquid stream (3) from 75:25 to 50:50, reduces the water content in the overhead vapor stream (5) withdrawn from the distillation column even further. For example, the water content in said overhead vapor stream obtained from the purification of acrolein can be reduced from ca. 7 wt.-% or more to less than 5 wt.-%.

By comparison, the process of US 2005/0103616 A1 gives an acrolein-rich gas mixture, which still contains 7 wt.-% of water. Accordingly, the process of US 2005/0103616 A1 gives acrolein with a lower degree of purity than the process according to the present invention.

In a preferred embodiment of the purification process according to the present invention the mass flow ratio of the first liquid stream (2) to the second liquid stream (3) ranges from 75:25 to 50:50.

In another embodiment of the purification process according to the present invention the temperature T2 of the second liquid stream (3) in step c) is 10° C. at the most.

A cooling of the second liquid stream (3) prior to its introduction into the distillation column (4) leads to a further improvement regarding the degree of purity of acrolein. Said cooling can be performed by means of the heat exchanger (9), and the thus cooled second liquid stream (3) is introduced into the distillation column (4) as liquid stream (10).

Preferably, the second liquid stream (3) is cooled prior to its introduction into the distillation column (4).

The purification process according to the present invention primarily avoids the reflux of a part of a condensed overhead vapor stream enriched in acrolein to the top the distillation column. The function of the reflux in standard distillation column is carried out by the second liquid stream (3). This leads to a reduction of the mass of the first liquid stream (2) compared to a standard distillation procedure. The lower mass of the first liquid stream (2) therefore can be heated up with less energy input compared to a standard distillation procedure, which leads to significant savings in the reboiler duty.

In addition, the process according to the present invention does not only save the energy consumption for an external condenser, which is otherwise required for providing the reflux in a standard distillation column, for example in the process of US 2005/0103616 A1, but it also saves the reboiler duty for the evaporation of the reflux within the distillation column.

One could speculate that cooling of the second liquid stream (3) prior to its introduction into the distillation column should lead to an increase in the reboiler duty because the capacity of the cooler (9) must be compensated by the reboiler of the distillation. However, it was found that a cooling of the second liquid stream (3) to a temperature T2 between 5 and 20° C. leads to an only insignificant increase in reboiler duty. Rather, the reboiler duty of the distillation column can be even decreased, when in addition to the cooling of the second liquid stream (3) and of any additional further streams, which are to be introduced along the rectifying section, the first liquid stream (2) is heated. Preferably, said first liquid stream (2) is heated to a temperature T1 of up to its boiling temperature. The first liquid stream (2), like the liquid feed stream (1), contains mainly water and approximately 5 to 6 wt.-% of acrolein. The boiling point of the stream (2) is therefore slightly below 100° C., approximately at 95° C. Therefore, the first liquid stream (2) is preferably heated to a temperature T1 of from more than 10° C. to 95° C., in particular to a temperature if from 15 to 95° C. or from 20 to 95° C.

In a further embodiment of the purification process according to the present invention the first liquid stream (2) is heated prior to its introduction into the distillation column (4).

The thus heated first liquid stream (2) is then introduced as stream (8) into the distillation column (4).

In a preferred embodiment of the purification process according to the present invention the first liquid stream (2) is heated to a temperature T1 of from more than 10° C. to 95° C.

Preferably, the first liquid stream (2) is heated to a temperature T1 of from 15° C. to 95° C. or from 20° C. to 95° C.

It is preferred that in the process according to the present invention the temperature T2 of the second liquid stream (3) in step c) is 10° C. at the most and the temperature T1 of the first liquid stream (2) in step b) ranges from more than 10° C. to 95° C.

For an optimized heat integration, it is preferred to heat the first liquid stream (2) by means of the bottom stream (6) from the distillation column (4). Said bottom stream has a high heat capacity, and therefore can transfer the most possible heat to the first liquid stream (2). This heating can be done in the heat exchanger (7). After having transferred heat to the first liquid stream (2) the thus cooled bottom stream (11) is sent to a further utilization. The stream (11) mainly contains water and if any, then only few ppm of heavy boilers as by-products from the distillation. However, the extremely low amount of these by-products does not have any impact on acrolein. Therefore, the cooled bottom stream (11) is preferably sent back to the absorption column in the preparation of acrolein, in which the acrolein is separated from the acrolein comprising gas stream by absorption in water.

In another preferred embodiment of the purification process according to the present invention the first liquid stream (2) is heated by heat exchange with the bottom stream (6) from the distillation column (4).

The use of a reduced pressure in the process according to the present invention leads to a further improvement regarding the safety of the process and the degree of purity of the acrolein. Regarding safety, the use of a reduced pressure in the process according to the present invention has the benefit that no acrolein escapes from the distillation column (4) or from a line leading the overhead vapor stream to a further processing in case of a leakage of the distillation column (4) or of said line.

Rather, air is soaked into the apparatus. The use of a reduced pressure has the additional benefit, that the temperatures in the distillation column (4) decrease, which also leads to less fouling in said column.

In one embodiment the purification process according to the present invention is therefore performed under reduced pressure.

In a preferred embodiment the purification process according to the present invention is performed at a pressure of from 400 to 800 mbara.

In particular, the purification process according to the present invention is performed at a pressure of from 500 to 650 mbara.

According to the present invention the first liquid stream (2) is introduced at a point between the top and the bottom of the distillation column (4). This particular point is often also referred to as feed stage. The feed stage is preferably chosen to be in the upper end of the middle third of the distillation column, i.e. it is a point of the upper end of the middle third of the separation stages (theoretical stages) of a distillation column. Therefore, said indication of the feed stage applies to all types of distillation columns, such as a trayed column, a packed column, or a column with a structured packing. Preferably, said feed stage is chosen to provide from 40 to 80%, in particular from 50 to 75%, of the separation stages of the distillation column (4) in the stripping section and the remainder in the rectifying section. For example, when a distillation column has 14 separation stages, with the $1^{st}$ separation stage at the top and the $14^{th}$ separation stage at the bottom, the liquid feed stream (1) is introduced at the $5^{th}$ separation stage. However, the process according to the present invention is not subject to any limitations regarding the number of streams into which the stream (1) is split and which are introduced into the distillation column. Hence, the process according to the present invention is also not subject to any limitations regarding the number of further streams in addition to the first liquid stream (2), which are also introduced at a point along the distillation column. When the liquid feed stream (1) is split into more than two streams, the one or more streams in addition to the first liquid stream (2) is/are preferably introduced at a point along the rectifying section of the distillation column, which is different from the point of introduction of the first liquid stream (2). Preferably, this further stream in addition to the first liquid stream (2) is introduced at a point between the top and the bottom of the distillation column (4), which is different from the introduction of stream (2), in particular at a point between the points of introduction of the first liquid stream (2) and the second liquid stream (3). It is further preferred, that said further stream is introduced into the distillation column with a temperature T3 between the temperature T1 of the first liquid stream (2) upon introduction into the distillation column and the temperature T2 of the second liquid stream (3) upon introduction into the distillation column.

In an embodiment the purification process according to the present invention further comprises the step of f) introducing at least one further liquid stream in addition to the first liquid stream (2) into the distillation column (4) at a point between the points of introduction of the first liquid stream (2) and the second liquid stream (3), wherein the temperature T3 of the further stream is between the temperature T2 of the second stream (3) in step c) and the temperature T1 of the first liquid stream (2) in step b).

In a preferred embodiment of the purification process according to the present invention, the first liquid stream (2) is introduced into the distillation column in step b) at a larger mass flow ratio than the at least one further stream, which is introduced into said distillation column in addition to the first liquid stream (2).

In principle, the process according to the present invention aims at avoiding the condensing of at least a part or all of the overhead vapor stream (5) enriched in acrolein and the feeding of the thus liquefied stream back as reflux to the top of the distillation column (4). Thus, in step d) said overhead vapor stream (5) enriched in acrolein is not condensed after being withdrawn from the distillation column (4). Accordingly, said overhead vapor stream (5) may be further processed without any condensation after being withdrawn from the distillation column (4).

In yet a further embodiment of the purification process according to the present invention the overhead vapor stream (5) withdrawn from the distillation column (4) is further processed without any condensation of said vapor stream.

Figure 3:
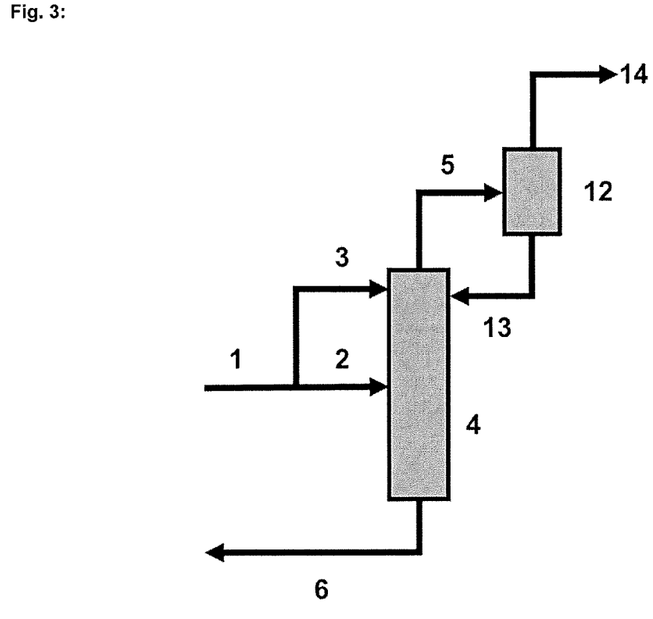
FIG. 3 shows an embodiment of the process of the invention where a part of overhead vapor stream (5) withdrawn from distillation column (4) is condensed to give a liquefied stream (13) and a residual vapor stream (14).
Figure 4:
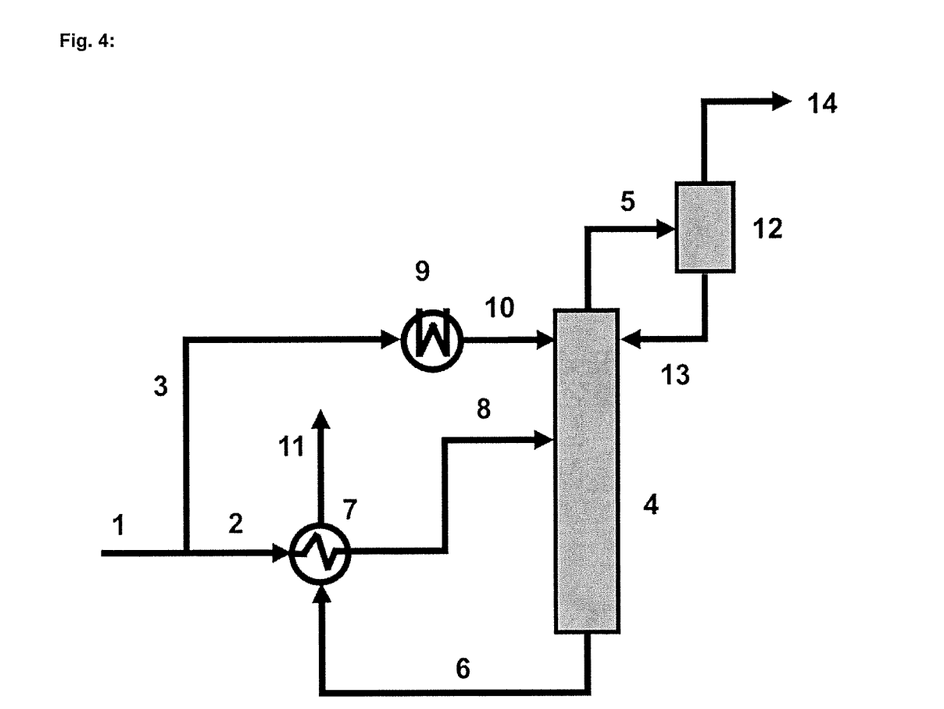
FIG. 4 shows an embodiment of the process of the invention combining the features shown in FIGS. 2 and 3.

Nevertheless, at least a part of the overhead vapor stream (5) after being withdrawn from the distillation column (4) may be alternatively condensed to give a liquefied stream (13), which is fed back as reflux into the distillation column at the top of distillation column, and a residual vapor stream (14) as the non-condensed part of the overhead vapor stream (5). Accordingly, the residual vapor stream (14), which makes up the major part of the overhead vapor stream (5), is fed to a further processing without any condensation. The partial condensation of the overhead vapor stream (5) is performed in a condenser or partial-condenser (12). Accordingly, only a part but not the whole overhead vapor stream is fed to a condenser in this hybrid variant of the process according to the present invention, in contrast to the processes of the prior art, for example the process of US 2005/0103616 A1. Therefore, the partial liquefaction in the hybrid variant of the process according to the present invention, also gives a considerably smaller aqueous acrolein comprising condensate than in the processes of the prior art, for example the process of US 2005/0103616 A1.

In an alternative embodiment the purification process according to the present invention further comprises the steps of g) condensing a part of the overhead vapor stream (5) withdrawn from the distillation column (4) to give a liquefied stream (13) and a residual vapor stream (14), and h) feeding at least a part of the liquefied stream (13) of step g) as reflux back into the distillation column (4) at the top of said distillation column.

When the overhead vapor stream (5) is not completely condensed in step g), the non-condensed part of the overhead vapor stream (5), which makes up the vapor stream (14), is fed directly, i.e. without any condensation, to a further processing. Alternatively, when the overhead vapor stream (5) is completely condensed in step g) to give a liquefied stream (13), it is fed to a further processing or to a storage tank in step h).

In order to provide for the beneficial safety and energy effects of the process according to the present invention the liquefied stream (13), fed back as reflux to the distillation column, is preferably kept relatively low or as small as possible. In any case, the liquefied stream (13) is fed back in step (h) as reflux to the top of the distillation column at a smaller mass flow than the mass of the stream (3) introduced at the top of the distillation column. Preferably, 5 wt.-%, 10 wt.-%, 15 wt.-%, 20 wt.-%, 25 wt.-%, 30 wt.-%, 35 wt.-%, 40 wt.-%, 45 wt.-% or less than 50 wt.-% of the overhead vapor stream (5) is condensed in step g) and fed back as reflux to the top of the distillation column. In order to keep the mass stream of the liquefied stream (13), fed back as reflux to the distillation column, as small as possible, the mass flow ratio of the liquefied stream (13) to the stream (3) is preferably adjusted to a ratio of from 5:95 to 45:55, from 5:95 to 40:60, from 5:95 to 35:65, from 5:95 to 30:70 or from 5:95 to 25:75. That part of the liquefied stream (13), which is not fed back as reflux to the distillation column can be fed to a further processing or to a storage tank.

In a preferred alternative embodiment of the purification process according to the present invention the liquefied stream (13) is fed back as reflux to the top of the distillation column at a smaller mass flow than the second liquid stream (3) introduced at the top of the distillation column.

In a further preferred alternative embodiment of the purification process according to the present invention the mass flow ratio of the liquefied stream (13) to the second liquid stream (3) ranges from 5:95 to 45:55.

Figure 5:
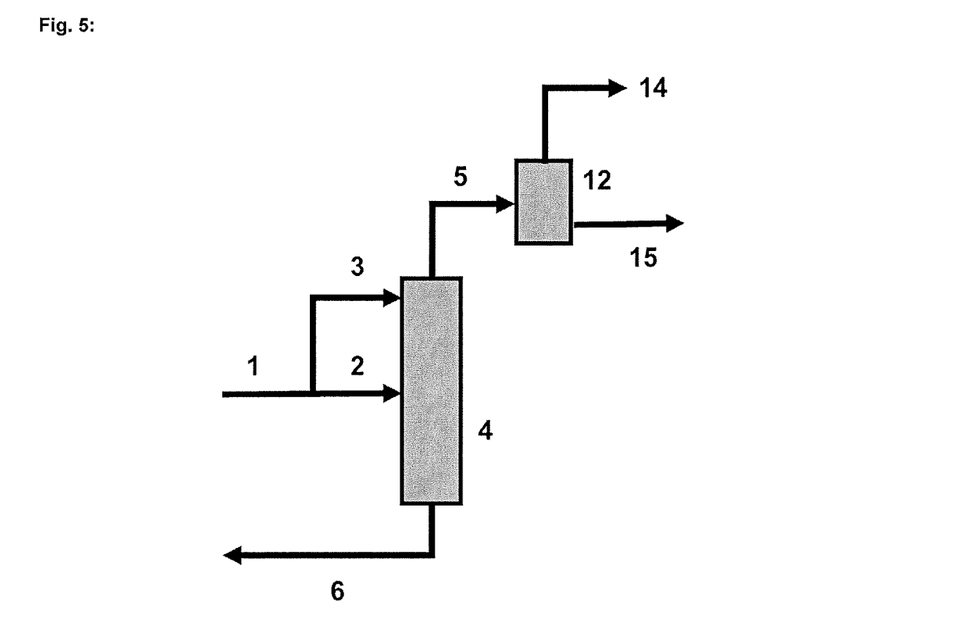
FIG. 5 shows another embodiment of the process of the invention where at least a part of the overhead vapor stream is condensed to give a liquefied stream (15), which is to be fed to further processing or storage tank, and, if applicable, a residual vapor stream (14).
Figure 6:
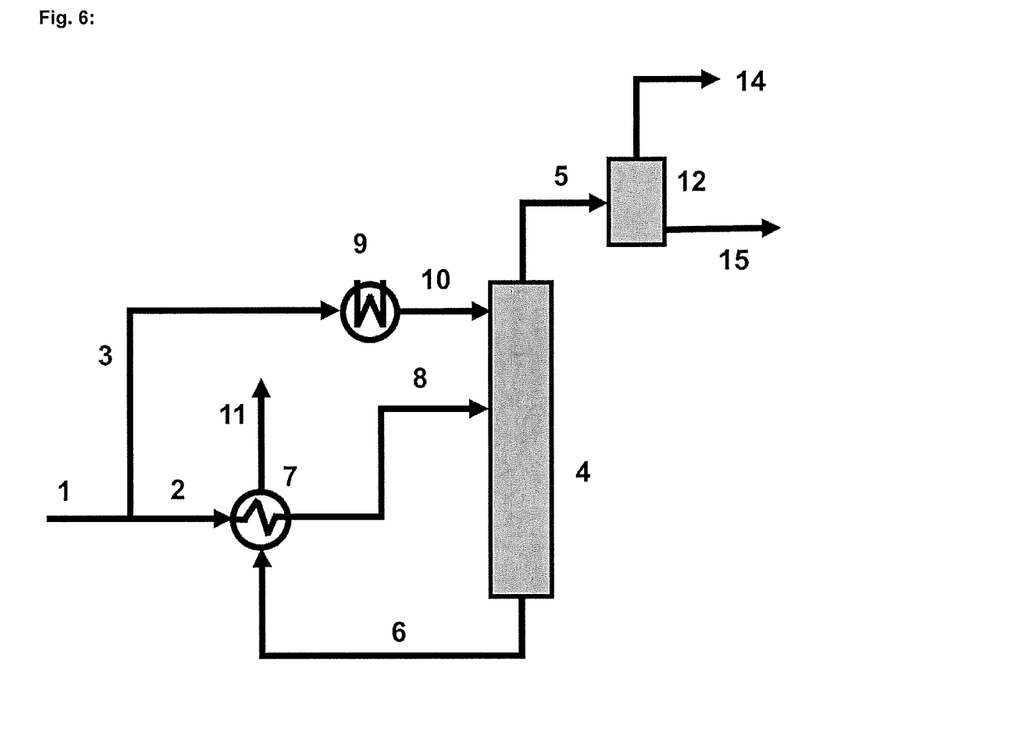
FIG. 6 shows an embodiment of the process of the invention combining the features shown in FIGS. 4 and 5.
Figure 7:
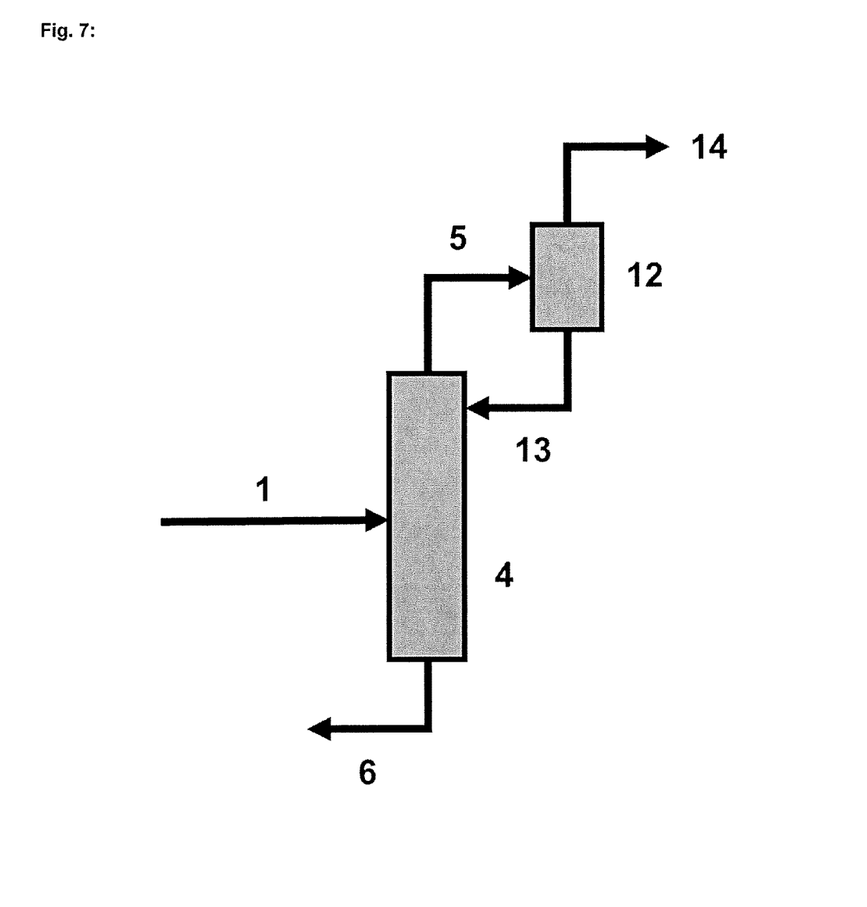
FIG. 7 shows a prior art process for the purification of acolein where feed stream (1) is introduced at the feed stage of the distillation column (4), the overhead vapor stream (5) withdrawn from distillation column (4) is partially condensed to give residual vapor stream (14) and liquefied stream (13) is fed back to distillation column (4) as reflux.

As explained above in detail, the purification process according to the present invention leads to a reduction of the holdup of liquid acrolein in a distillation apparatus and therefore, an overhead vapor stream (5) enriched in acrolein is withdrawn from the distillation column. However, due to fluctuations in productions, it is not always possible to further process or react said overhead vapor stream (5) or the residual vapor stream (14), also enriched in acrolein, directly as obtained from step d) of the process according to the present invention. It is therefore beneficial to liquefy all or part of the overhead vapor stream (5) withdrawn from the distillation column (4) to give a liquefied stream (15), which can be stored easier than a vapor stream, and, if applicable, a residual vapor stream (14). Said residual vapor stream, if applicable, can be fed directly to a further processing. Preferably, the overhead vapor stream (5) withdrawn from the distillation is completely condensed to give the liquefied stream (15), which is fed to a further processing or storage tank. Another benefit of the liquefaction of the overhead vapor stream (5) withdrawn from the distillation column (4) is that the thus obtained liquid stream (15) can be easier handled and in particular easier metered to a reaction than a vapor stream.

In another alternative embodiment the purification process according to the present invention further comprises the steps of g') condensing at least a part of the overhead vapor stream (5) withdrawn from the distillation column (4) to give a liquefied stream (15) enriched in acrolein, and, if applicable, a residual vapor stream (14), and h') feeding the liquefied stream (15) of step g') to a further processing or to a storage tank.

A further improvement regarding safety aspects is achieved when the overhead vapor stream (5) enriched in acrolein, the liquefied stream (15) enriched in acrolein and/or the residual vapor stream (14) enriched in acrolein and obtained by the purification process according to the present invention, is/are converted as soon as possible, preferably directly, into a less hazardous compound. This avoids the holdup of concentrated liquid acrolein completely and also reduces the risk potential of acrolein significantly. From an economic point of view, the thus obtained acrolein derived compound should be a relevant final or intermediate product. In case of an intermediate product, said acrolein derived compound should be easily convertible into other compounds of economic relevance. Acrolein is an important starting compound in the production of the essential amino acid D,L-methionine and in this process acrolein is converted to 3-methylmercaptopropion-aldehyde by reaction with methylmercaptan. 3-methylmercaptopropionaldehyde is an important intermediate product in the preparation of D,L-methionine, in which it is converted to an hydantoin by reaction with hydrogen cyanide. The thus obtained hydantoin is hydrolyzed in basic solution to give a methionate, which is precipitated from the solution as free methionine by carbonizing said solution, i.e. by introducing carbon dioxide into the solution.

Without wishing to be bound to a specific theory, it is believed that there are also other compounds present in a solution containing acrolein, methylmercaptan and the 3-methylmercaptopropion-aldehyde formed by the direct reaction of acrolein with methylmercaptan. Specifically, it is believed that the 3-methylmercaptopropionaldehyde further reacts with methylmercaptan to give the corresponding hemithioacetal, i.e. 1,3-bis(methylthio)-1-propanol. However, said hemithioacetal is present in equilibrium with its individual starting compounds 3-methylmercaptopropionaldehyde and methylmercaptan. It is therefore believed that acrolein, which is introduced into a reaction solution of acrolein with methylmercaptan and reaction product, does not only or primarily react with the initially provided methylmercaptan but also with the methylmercaptan present in equilibrium with the hemithioacetal. Accordingly, when acrolein reacts with methylmercaptan under formation of 3-methylmercaptopropionaldehyde, so that the solution becomes depleted in methylmercaptan, said methylmercaptan is provided again from the equilibrium with the hemithioacetal.

The published patent application US 2012/0165573 A1 already discloses the reaction of gaseous acrolein with a liquid mixture comprising 3-methylmercaptanpropionaldehyde, methyl mercaptan, the thiohemiacetal, which is formed of methyl mercaptan and 3-methylmercaptanpropionaldehyde, and a catalyst. However, the process disclosed in this document involves the use of a crude product gas from the acrolein production by oxidation of propene, which therefore only contains ca. 6.4 vol.-% of acrolein. The other components in said crude acrolein product gas do not contribute to any additional benefit in the preparation of 3-methylmercaptanpropionaldehyde. Rather, they lead to very large substance stream, whose heating and conducting throughout the process requires a large apparatus design and a large energy input. This, however, makes the process of US 2012/0165573 A1 rather unattractive from both an energy and an economic point of view. By comparison, the purification process according to the present invention allows to use acrolein enriched vapor streams, i.e. the overhead vapor stream (5) or the vapor stream (14), in the preparation of 3-methylmercaptopropionaldehyde by reacting one of these streams with methyl mercaptan, the hemithioacetal of methyl mercaptan and 3-methylthiomercaptopropionaldehyde and/or a mixture thereof. The process for the preparation of 3-methylthiomercaptopropionaldehyde according to the present invention therefore allows the preparation of this product with a higher purity and less energy input than in the process of US 2012/0165573 A1. The published patent application US 2014/005437 A1 also discloses an integrated method for producing acrolein and 3-methylmercaptopropionaldehyde. However, regarding the purification of the acrolein, the process according to the technical teaching of this document involves the use a standard distillation column and the condensation of the whole acrolein containing distillate from the distillation. Accordingly, the process of US 2014/005437 A1 is not suitable to reduce the holdup of liquid acrolein in the purification by distillation of acrolein.

Another object of the present invention is therefore a process for the preparation of 3-methylmercaptopropionaldehyde comprising the steps of
i) purifying a liquid feed stream (1) comprising acrolein in the process for the purification of acrolein according to the present invention to provide an overhead vapor stream (5) enriched in acrolein, a residual vapor stream (14), enriched in acrolein and/or a liquefied stream (15) enriched in acrolein, and
ii) reacting said overhead vapor stream (5) enriched in acrolein, said residual vapor stream (14) enriched in acrolein and/or said liquefied stream (15) enriched in acrolein with at least one of the group consisting of methyl mercaptan, the hemithioacetal of methyl mercaptan and 3-methylthiomercaptopropionaldehyde and a mixture thereof to give 3-methylmercaptopropionaldehyde.

It is a further benefit of this process for the preparation of 3-methyl-mercaptopropionaldehyde that methylmercaptan, another compound with a high risk potential, is converted to the significantly less hazardous compound 3-methylmercaptopropionaldehyde. Another benefit is the presence of 3-methylmercaptopropionaldehyde in liquid form at room temperature, in contrast to methylmercaptan, which is gas at room temperature. By comparison, methylmercaptan is a gas at room temperature, and due to its high risk potential, it must be stored in a special pressure tank. The preparation process according to the present invention allows to work without a pressure tank and under less strict safety regulations.

The reaction between acrolein and methylmercaptan is rather exotherm. In order to avoid any side-reactions of acrolein, in particular polymerization reactions of acrolein, it is preferred to perform step ii) of the process for the preparation of 3-methylmercaptopropionaldehyde in the presence of a solvent with a high boiling point. It is further preferred that said solvent with high boiling point in step ii) is 3-methylmercaptopropionaldehyde. The use of 3-methylmercaptopropionaldehyde as high boiling solvent in step ii) of the process also has the benefit that the reaction product itself is already used as solvent and thus, there is no need for a complicated and energy consuming process for the separation of the solvent from the reaction product. Therefore, the reaction product 3-methylmercaptopropionaldehyde is not subjected to any degradation or polymerization reactions, which otherwise may occur during the purification processes for 3-methylmercaptopropionaldehyde.

As far as the step i) of this additional object is concerned, all of the aforementioned embodiments of the purification process according to the present invention apply.

The present invention is further illustrated by the following figures and examples.

EXAMPLES

Figure 1:
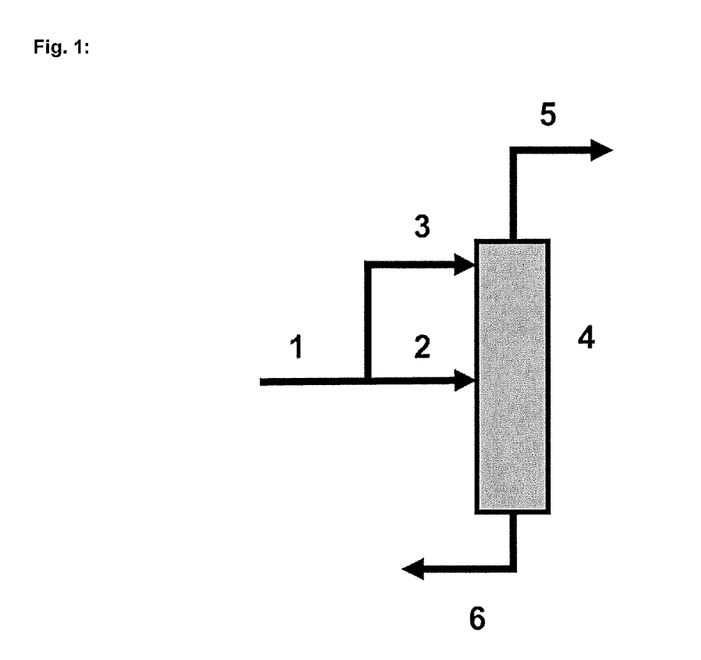
FIG. 1 is a schematic representation of a process for the purification of acrolein according to the present invention.
Figure 2:
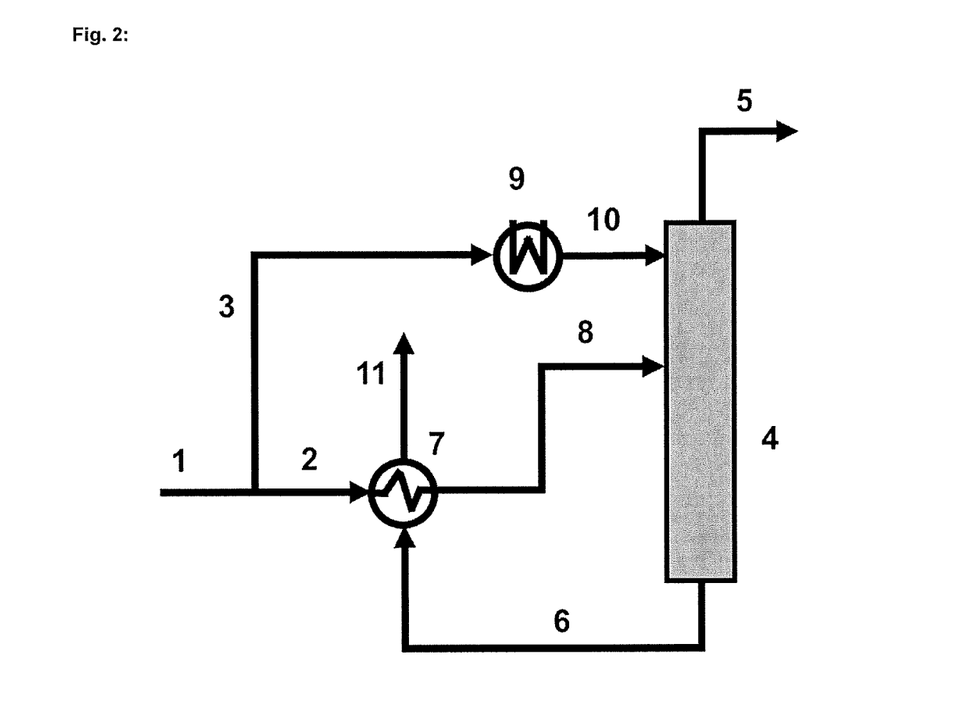
FIG. 2 shows an embodiment of the process of the invention where first liquid stream (2) is heated by heat exchange with bottoms stream (6) before it is introduced into distillation column (4).

The examples herein are performed using a computational model of a process based on the distillation process shown in FIG. 2. Process modelling is an established and reliable methodology used by engineers to simulate complex chemical processes before building the real plant. In the context of the examples herein the commercial modeling software Aspen Plus® (Aspen Technology, Inc., 20 Crosby Roads, Bedford, Mass. 01730, USA) was used in combination with physical property data available from public databases.

Example 1 Purification of an Acrolein Comprising Stream According to the Invention Using the modeling software Aspen Plus®, the purification of the acrolein comprising stream is simulated for a distillation process shown in FIG. 2: An aqueous feed stream (1) comprising ca. 6 wt.-% acrolein is split into a first liquid stream (2) and a second liquid stream (3) with a mass flow ratio of 85:25. The stream (2) is heated to a temperature of about 84° C. in the heat exchanger (7) by use of the bottom stream (6) from the distillation column (4) to give a heated stream (8). Said stream (8) is introduced at the feed stage of the distillation column (4). The heat transmitted in the heat exchanger (7) is kept at 9765 kW for all mass ratios of stream (2) to stream (3). The thus obtained cooled bottom stream (11) is discarded. The stream (3) is introduced at the highest stage of the distillation column (4) with a temperature of 18.5° C. A bottom stream (11) enriched in water is feed to the heat exchanger (7).

The water content in the gas stream (5) is influenced by the mass flow ratio of the first liquid stream (2) to the second liquid stream (3). Specifically, the water content is reduced from almost 8% to less than 5% by increasing the part of the stream (3) from 15 to 25 wt.-%, i.e. establishing a mass flow ratio of stream (2) to stream (3) of 75:25. At the same time the reboiler duty of the distillation column is reduced by almost 5% by increasing the part of the stream (3) from 15 to 25 wt.-%. A further increase of the part of the stream (3), however, does not result in a further reduction of the water content and/or of the reboiler duty. These results are summarized in the table 1 below.

TABLE 1

Influence of the split ratio of stream (2) to stream (3) on the water content in gas stream (5) and on the reboiler duty for desorption in the distillation column (4)

| Mass flow ratio of stream (2) to stream (3) | Water content in overhead vapor stream (5) [wt.-%] | Reboiler duty of distillation column (4) [kW] |
|---|---|---|
| 100:00 | 3.50 | 7142 |
| 85:15 | 7.80 | 6233 |
| 80:20 | 5.04 | 5972 |
| 75:25 | 4.83 | 5939 |
| 70:30 | 4.80 | 5935 |
| 65:35 | 4.79 | 5932 |
| 60:40 | 4.78 | 5932 |
| 55:45 | 4.78 | 5932 |
| 50:50 | 4.78 | 5930 |

A further reduction of the water content in the gas stream (5) from close to 5 wt.-% to almost 4 wt.-% is achieved by cooling the second liquid stream (3) in the cooler (9) to give a cooled stream (10), which is introduced at the highest stage of the distillation column (4). The required cooling capacity of the cooler (9) has to be compensated in the evaporator of the distillation column (4). Therefore, the reboiler duty in the distillation column (4) increases again, but only slightly (see table 2 for a constant split ratio of 75:25 of first liquid stream (2) to second liquid stream (3)).

TABLE 2

Influence of the temperature of stream (10) on the water content in the stream (5) and on the reboiler duty for desorption in the distillation column (4).

| Temperature of stream (10) [° C.] | Water content in overhead vapor stream (5) [wt.-%] | Reboiler duty of distillation column (4) [kW] |
|---|---|---|
| 5 | 4.22 | 6421 |
| 10 | 4.32 | 6226 |
| 15 | 4.56 | 6073 |
| 18.5 | 4.83 | 5939 |

Example 2 Comparative Example

For illustration of the benefits of the process according to the present invention, the experimental data of the purification of acrolein in a standard distillation known from the prior art were compared with simulation results for the purification of acrolein in a process according to the present invention. Said simulation involved a variation of the mass flow ratios of stream (2) to stream (3) and the temperatures of stream (10), i.e. cooled stream (3). The results summarized in table 3 show that the process according to the present invention gives acrolein with the same or at least comparable degree of purity as a prior art distillation process. However, the simulation data show that the process according to the present invention has a significantly lower energy consumption than the prior art distillation process.

TABLE 3

Comparison of the purification of acrolein in the process according to the present invention, entries 2 to 7, with a standard purification of acrolein according to the prior art, entry 1.

| Stream (2)/[m³/h] | Stream (3)/[m³/h] | T of stream (3)/[° C.] | Reflux (8)/[m³/h] | Water/ [wt.-%] | Reboiler duty/[kW] |
|---|---|---|---|---|---|
| 100 | 0 | — | 5.82 | 3.8 | 3599 |
| 84.18 | 15.82 | 18.3 | 0 | 4.5 | 3114 |
| 87.34 | 12.66 | 10 | 0 | 4.3 | 3195 |
| 87.34 | 12.66 | 15 | 0 | 5.6 | 3114 |
| 88.93 | 11.07 | 7.5 | 0 | 5.6 | 3195 |
| 89.24 | 10.76 | 5 | 0 | 4.8 | 3033 |
| 89.56 | 10.44 | 5 | 0 | 5.5 | 3073 |

In addition, an analysis was made for the accumulation of specific components in the rectifying section of a distillation column based on the simulation results for the purification of acrolein in a process according to the present invention and the experimental data for the purification of acrolein in a standard distillation of the prior art. The results are summarized in the table 4. Specifically, it was found that the process according to the present invention leads to a significant reduction in the holdup of concentrated acrolein in the distillation apparatus, in particular in the distillation column, compared to a standard distillation process. It was further found, that the process according to the present invention suppresses or at least significantly reduces the accumulation of other components, which typically accumulate during the purification of acrolein comprising solutions in a standard distillation process of the prior art.

TABLE 4

Comparison of the accumulation of by-products in purification of acrolein in the process according to the present invention and in a standard purification of acrolein according to the prior art.

| Component in rectifying section | Purification of acrolein in standard distillation process | Purification of acrolein in process according to invention |
|---|---|---|
| liquid acrolein | 95 wt.-% | 18 wt.-% |
| liquid allylalcohol | 2.5 wt.-% | <0.1 wt.-% |
| liquid acrylacrylate | 7.0 wt.-% | 0 |
| liquid acrylic acid | 0 | 0 |
| liquid formaldehyde | 0.3 wt.-% | 0.3 wt.-% |

LIST OF REFERENCE SIGNS (1) liquid feed stream comprising acrolein
(2) first liquid split stream to be introduced into the distillation column (4) at a point between the top and the bottom section of the distillation column (4)
(3) second liquid split stream to be introduced into the distillation column (4) at the top of the distillation column (4)
(4) distillation column
(5) overhead vapor stream enriched in acrolein
(6) bottom stream depleted in acrolein
(7) heat exchanger for heating first liquid stream (2)
(8) heated stream from the heat exchanger (7) to be introduced into the distillation column (4) at a point between the top and the bottom of the distillation column (4)
(9) heat exchanger for cooling second liquid stream (3)
(10) cooled stream from heat exchanger (9) to be introduced at the top of the distillation column (4)

(11) bottom stream from heat exchanger (7)
(12) (partial) condenser for overhead vapor stream (5)
(13) liquefied stream from (partial) condenser (12) to be fed back as reflux to distillation column
(14) residual vapor stream to be fed to further processing
(15) liquefied stream to be fed to further processing or storage tank.

The invention claimed is:

1. A process for purifying acrolein, the process comprising
   a) splitting a liquid feed stream comprising acrolein into at least a first liquid stream and a second liquid stream,
   b) introducing the first liquid stream with a temperature T1 into a distillation column at a point between the top and the bottom of the distillation column,
   c) introducing the second liquid stream with a temperature T2 into the distillation column at the top of the distillation column,
   d) withdrawing an overhead vapor stream enriched in acrolein from the distillation column, and
   e) withdrawing a bottom stream depleted in acrolein from the distillation column,
   wherein the temperature T2 of the second liquid stream in said introducing c) is lower than the temperature T1 of the first liquid stream in said introducing b).

2. The process according to claim 1, wherein a mass flow ratio of the first liquid stream to the second liquid stream ranges from 95:5 to 50:50.

3. The process according to claim 1, wherein a mass flow ratio of the first liquid stream to the second liquid stream ranges from 75:25 to 50:50.

4. The process according to claim 1, wherein the temperature T2 of the second liquid stream in said introducing c) is 10° C. at the most.

5. The process according to claim 1, wherein the first liquid stream is heated prior to its introduction into the distillation column.

6. The process according to claim 5, wherein the first liquid stream is heated to the temperature T1 of from more than 10° C. to 95° C.

7. The process according to claim 5, wherein the first liquid stream is heated by heat exchange with the bottom stream from the distillation column.

8. The process according to claim 1, wherein the process is performed under reduced pressure.

9. The process according to claim 1, wherein the process is performed at a pressure of from 400 to 800 mbara.

10. The process according to claim 1, wherein the overhead vapor stream withdrawn from the distillation column is further processed without any condensation of said vapor stream.

11. The process according to claim 1, further comprising
    g) condensing a part of the overhead vapor stream withdrawn from the distillation column to give a liquefied stream and a residual vapor stream, and
    h) feeding at least a part of the liquefied stream as reflux back into the distillation column at the top of said distillation column.

12. The process according to claim 11, wherein the liquefied stream is fed back as reflux to the top of the distillation column at a smaller mass flow than the mass and/or volume of the second liquid stream introduced at the top of the distillation column.

13. The process according to claim 12, wherein a mass flow ratio of the liquefied stream to the second liquid stream ranges from 5:95 to 45:55.

14. The process according to claim 1, further comprising
    g') condensing at least a part of the overhead vapor stream withdrawn from the distillation column to give a liquefied stream, and, if applicable, a residual vapor stream, and
    h') feeding the liquefied stream to a further processing or to a storage tank.

15. A process for preparing 3-methylmercaptopropionaldehyde, the process comprising
    i) purifying the liquid feed stream comprising acrolein by the process according to claim 1 to provide the overhead vapor stream enriched in acrolein, a residual vapor stream, enriched in acrolein and/or a liquefied stream enriched in acrolein, and
    ii) reacting said overhead vapor stream enriched in acrolein, said residual vapor stream, enriched in acrolein and/or said liquefied stream enriched in acrolein with at least one selected from the group consisting of methyl mercaptan, the hemithioacetal of methyl mercaptan and 3-methylthiomercaptopropionaldehyde to give 3-methylmercaptopropionaldehyde.

\* \* \* \* \*